(12) United States Patent
Wardlaw et al.

(10) Patent No.: US 8,310,659 B2
(45) Date of Patent: Nov. 13, 2012

(54) METHOD AND APPARATUS FOR DETECTING AND COUNTING PLATELETS INDIVIDUALLY AND IN AGGREGATE CLUMPS

(75) Inventors: Stephen C. Wardlaw, Lyme, CT (US); Robert A. Levine, Guilford, CT (US); Niten V. Lalpuria, Hamden, CT (US)

(73) Assignee: Abbott Point of Care, Inc., Princeton, NJ (US)

( * ) Notice: Subject to any disclaimer, the term of this patent is extended or adjusted under 35 U.S.C. 154(b) by 0 days.

(21) Appl. No.: 13/323,438

(22) Filed: Dec. 12, 2011

(65) Prior Publication Data

US 2012/0147357 A1 Jun. 14, 2012

Related U.S. Application Data

(63) Continuation of application No. 13/088,853, filed on Apr. 18, 2011, now Pat. No. 8,077,296, which is a continuation of application No. 12/408,500, filed on Mar. 20, 2009, now Pat. No. 7,929,121.

(60) Provisional application No. 61/038,554, filed on Mar. 21, 2008.

(51) Int. Cl.
*G01N 33/48* (2006.01)
(52) U.S. Cl. ............................................ 356/39; 356/40
(58) Field of Classification Search ............... 356/39–42
See application file for complete search history.

(56) References Cited

U.S. PATENT DOCUMENTS

| | | | |
|---|---|---|---|
| 4,023,716 A | 5/1977 | Shapiro | |
| 4,197,088 A | 4/1980 | Meserol et al. | |
| 4,487,081 A | 12/1984 | De Vaughn et al. | |
| 4,615,878 A | 10/1986 | Kass | |
| 5,012,818 A | 5/1991 | Joishy | |
| 5,068,181 A | 11/1991 | Driscoll | |
| 5,192,511 A | 3/1993 | Roach | |
| 5,284,771 A | 2/1994 | Fan et al. | |
| 5,447,838 A | 9/1995 | Meiklejohn et al. | |
| 5,454,268 A | 10/1995 | Kim | |
| 5,460,782 A | 10/1995 | Coleman et al. | |

(Continued)

FOREIGN PATENT DOCUMENTS

DE 10011235 9/2001

(Continued)

OTHER PUBLICATIONS

Sun et al, "Microminiaturized immunoassays using quantum dots as fluorescent label by laser confocal scanning fluorescence detection," Journal of Immunological Methods, Elsevier Science Publishers, vol. 249, No. 1-2, pp. 85-89, Mar. 2001.

(Continued)

*Primary Examiner* — Michael P Stafira
(74) *Attorney, Agent, or Firm* — O'Shea Getz P.C.

(57) ABSTRACT

A method for enumerating platelets within a blood sample is provided. The method includes the steps of: 1) depositing the sample into a sample container having an analysis chamber adapted to quiescently hold the sample for analysis, and an amount of colorant that platelets absorb and which fluoresces upon exposure to one or more predetermined first wavelengths of light; 2) imaging at least a portion of the sample disposed in the analysis chamber, including producing image signals indicative of fluorescent emissions from the platelets illuminated by first wavelengths of light; 3) identifying the platelets using the image signals; and 4) enumerating individual platelets and clumped platelets within the sample using one or more of fluorescent emissions, area, shape, and granularity.

11 Claims, 8 Drawing Sheets

U.S. PATENT DOCUMENTS

| | | | |
|---|---|---|---|
| 5,739,042 A | 4/1998 | Frengen | |
| 5,768,407 A | 6/1998 | Shen et al. | |
| 5,770,160 A | 6/1998 | Smith et al. | |
| 6,127,184 A | 10/2000 | Wardlaw | |
| 6,235,536 B1 | 5/2001 | Wardlaw | |
| 6,346,421 B1 | 2/2002 | Anderson et al. | |
| 6,350,613 B1 | 2/2002 | Wardlaw et al. | |
| 6,723,290 B1 | 4/2004 | Wardlaw | |
| 6,730,521 B1 | 5/2004 | Cassells | |
| 6,866,823 B2 | 3/2005 | Wardlaw | |
| 6,919,960 B2 | 7/2005 | Hansen et al. | |
| 7,068,365 B2 | 6/2006 | Hansen et al. | |
| 7,796,797 B2 | 9/2010 | Nakaya et al. | |
| 2002/0028158 A1 | 3/2002 | Wardlaw | |
| 2002/0131902 A1 | 9/2002 | Levy | |
| 2003/0025896 A1 | 2/2003 | Oever et al. | |
| 2003/0224534 A1 | 12/2003 | Kawate | |
| 2004/0048330 A1 | 3/2004 | Bittner | |
| 2004/0165090 A1 | 8/2004 | Ning | |
| 2005/0002826 A1 | 1/2005 | Oguni et al. | |
| 2005/0026197 A1 | 2/2005 | Dertinger | |
| 2005/0277159 A1 | 12/2005 | Lehmann et al. | |
| 2006/0159962 A1 | 7/2006 | Chandler et al. | |
| 2006/0258018 A1 | 11/2006 | Curl et al. | |
| 2007/0087442 A1 | 4/2007 | Wardlaw | |
| 2007/0243117 A1 | 10/2007 | Wardlaw | |
| 2008/0070317 A1 | 3/2008 | Bradshaw et al. | |

FOREIGN PATENT DOCUMENTS

| | | | |
|---|---|---|---|
| DE | 10240742 | 3/2004 | |
| EP | 0366151 | 5/1990 | 33/543 |
| EP | 0642829 | 3/1995 | |
| EP | 1239284 | 9/2002 | 33/53 |
| GB | 2254414 | 10/1992 | 21/84 |
| WO | WO 9802727 | 1/1998 | 15/14 |
| WO | WO 0057891 | 5/2000 | |
| WO | WO 0223154 | 3/2002 | 33/558 |

OTHER PUBLICATIONS

Goldman et al., "Multiplexed Toxin Analysis using Four Colors of Quantum Dot Fluororeagents," Analytical Chemistry, American Chemical Society, vol. 76, No. 3, pp. 684-688, Feb. 2004.

Matzdorff et al., "Quantitative assessment of platelets, platelet microparticles, and platelet aggregates in flow cytometry," The Journal of Laboratory and Clinical Medicine, vol. 131, No. 6, pp. 507-517, Jun. 1998.

Hu Hu et al, "Effects of insulin on platelet and leukocyte activity in whole blood," Thrombosis Research, vol. 107, No. 5, pp. 209-215, Sep. 2002.

Sbrana et al., "Relationships between optical aggregometry (type born) and flow cytometry in evaluating ADP-induced platelet activation," Cytometry, Part B, Clinical Cytometry, vol. 74, No. 1, pp. 30-39, Jan. 2008.

METHOD AND APPARATUS FOR DETECTING AND COUNTING PLATELETS INDIVIDUALLY AND IN AGGREGATE CLUMPS

The present application is a continuation of U.S. patent application Ser. No. 13/088,853 filed Apr. 18, 2011, which is a continuation of U.S. Pat. No. 7,929,121 filed Mar. 20, 2009, which claims priority to U.S. Provisional Patent Appln. No. 61/038,554, filed Mar. 21, 2008.

BACKGROUND OF THE INVENTION

1. Technical Field

The present invention relates to apparatus and methods for analysis of blood samples in general, and apparatus and methods for detecting and enumerating platelets, and differentiating platelets from giant platelets, and giant platelets from platelet clumps, in particular.

2. Background Information

Physicians, veterinarians and scientists have examined human and animals' biologic fluids, especially blood, in order to determine constituent quantities as well as to identify the presence of unusual particulates not seen in healthy subjects. The constituents generally measured, quantified and identified include red blood cells (RBCS), white blood cells (WBCs), and platelets.

In mammals, platelets (also referred to as thrombocytes) are small irregularly shaped anuclear cell fragments that are derived from fragmentation of megakaryocytes. Thrombocytes in certain animals (e.g., birds, reptiles and fish) are similar in function to mammalian platelets, but are about ten times larger and nucleated. Platelet analyses can include the number, size, shape, texture, and volume determinations of the platelets within the sample, including the determination of the presence of clumps of platelets or thrombocytes within the sample. Under certain naturally occurring conditions, platelets will aggregate into clumps within a subject as a useful response to a trauma (e.g., hemorrhaging, tissue trauma, etc.) experienced by the body. Platelet clumps forming within a blood sample collected for analysis, on the other hand, are typically not useful and can hinder the analysis of the blood sample. Anticoagulants (e.g., EDTA) can be used to prevent platelets from clumping within a sample, but clumps may still form if there is delay in mixing the anticoagulant with the blood sample. Once clumps form, anticoagulants are typically ineffective in separating them into individual platelets. Platelet clumps are often problematic within a sample being analyzed because they can lead to erroneously low platelet counts, which can lead to misdiagnosis and serious consequences to the patient.

Known blood examination techniques, described in detail medical texts such as Wintrobe's Clinical Hematology 12th Edition, generally divide the examination methods into manual, centrifugal, and impedance type methods. Manual methods typically involve the creation of an accurately determined volume of a blood or fluid sample that is quantitatively diluted and visually counted in a counting chamber. Manual examination methods for cell enumeration include examining a peripheral smear where the relative amounts of the particulate types are determined by visual inspection. Centrifugal examination methods involve centrifuging the sample, causing the sample to separate into constituent layers according to the relative densities of the constituents. The component layers can be stained to enhance visibility or detection. Impedance methods involve the examination of an accurate volume of blood which is treated according to the particulate being measured; e.g., lysing RBCs for enumeration of the nucleated cells and volumetrically diluting the sample in a conductive fluid. The process typically involves monitoring a current or voltage applied to sample passing through a narrow passage to determine the effect particulates have on the current/voltage as the particulates pass through in single file. Other techniques involve analyzing the intensity and angle of scatter of light incident to particulates passing single file through a light beam. Flow cytometric methods can also be used that involve staining particulates of interest in suspension with fluorophores attached to antibodies directed against surface epitopes present on cell or particle types, exciting the stained particulates with light of appropriate wavelengths, and analyzing the emission of the individual particulates/cells.

All of the aforementioned methods, other than the peripheral smear or centrifugal separation, require dispensing a precise volume of sample. Inaccuracies in the sample volume will result in quantitative errors of the same magnitude in the associated analysis. With the exception of centrifugal methods, all of the aforementioned methods also require the sample to be mixed with one or more liquid reagents or diluents, and also require calibration of the instrument to obtain accurate results. In the case of peripheral smears, a high degree of training is needed to properly examine the smear. A number of the aforementioned methods generate large volumes of contaminated waste which is expensive to handle. Additionally, the above-described methods are not suitable to determine the complete blood count (CBC) in birds, reptiles and fish, where the red blood cells and thrombocytes are nucleated, and in certain mammals where the red blood cells size is very small and may be confused with platelets.

SUMMARY OF THE INVENTION

According to an aspect of the present invention, a method for enumerating platelets within a substantially undiluted blood sample is provided. The method includes the steps of: 1) depositing the sample into an analysis chamber adapted to quiescently hold the sample for analysis, the chamber defined by a first panel and a second panel, both of which panels are transparent; 2) admixing a colorant with the sample, which colorant is operative to cause the platelets to fluoresce upon exposure to one or more predetermined first wavelengths of light; 3) illuminating at least a portion of the sample containing the platelets at the first wavelengths; 4) imaging the at least a portion of the sample, including producing image signals indicative of fluorescent emissions from the platelets, which fluorescent emissions have an intensity; 5) identifying the platelets by their fluorescent emissions, using the image signals; 6) determining an average fluorescent emission intensity value for the individual platelets identified within the at least a portion of the sample; 7) identifying clumps of platelets within the at least a portion of the sample using one or more of their fluorescent emissions, area, shape, and granularity; and 8) enumerating platelets within each platelet clump using the average fluorescent emission intensity value determined for the individual platelets within the sample.

An advantage of the present invention is that it provides an accurate platelet count within a blood sample. Most prior art hematology analyzers count the number of platelets within the sample by assuming that constituents within the sample of a certain size are in fact platelets. Giant platelets and platelet clumps, both of which are bigger than normal size platelets, may not therefore be considered in the count and may be counted as white blood cells. The resultant lower platelet count can be erroneously interpreted as a thrombocytopenia.

The present invention identifies giant platelets and platelet clumps and enumerates the platelets within the platelet clumps. As a result, a platelet count is provided that is more accurate than that provided by most prior art automated hematology analyzers and one which avoids counting giant platelets and platelet clumps as white blood cells resulting in falsely low platelet counts and falsely high white blood cell counts.

Another advantage of the present invention is that it permits the identification and enumeration of giant platelets within a blood sample.

Another advantage of the present invention is that it can be used to determine characteristics of a blood sample using an extremely small sample volume that may be obtained directly from the patient by capillary puncture rendering it more useful for point of care applications or from a venous sample if desired.

Another advantage of the present method is that it operates free of external and internal fluidics, and independent of gravity or orientation, and therefore is adaptable for use in a portable or hand held device and in microgravity conditions.

The present method and advantages associated therewith will become more readily apparent in view of the detailed description provided below, including the accompanying drawings.

BRIEF DESCRIPTION OF THE DRAWINGS

The application file contains at least one drawing executed in color. Copies of this patent or patent application publication with color drawing(s) will be provided by the Office upon request and payment of the necessary fee.

DETAILED DESCRIPTION OF EMBODIMENTS OF THE INVENTION

The present method generally utilizes an analysis chamber that is operable to quiescently hold a sample of substantially undiluted anticoagulated whole blood for analysis. The chamber is typically sized to hold about 0.2 to 1.0 µA of sample, but the chamber is not limited to any particular volume capacity, and the capacity can vary to suit the analysis application. The phrase "substantially undiluted" as used herein describes a blood sample which is either not diluted at all or has not been diluted purposefully, but has had some reagents added thereto for purposes of the analysis. To the extent the addition of the reagents dilutes the sample, if at all, such dilution has no clinically significant impact on the analysis performed. Typically, the only reagents that will be used in performing the present method are anticoagulants (e.g., EDTA, heparin) and colorants. These reagents are generally added in dried form and are not intended to dilute the sample. Under certain circumstances (e.g., very rapid analysis—such as may happen when blood is drawn from a patient finger stick or a neonatal heel-stick), it may not be necessary to add the anticoagulating agent, but it is preferable to do so in most cases to ensure the sample is in a form acceptable for analysis. The term "quiescent" is used to describe that the sample is deposited within the chamber for analysis, and is not purposefully moved relative to the chamber during the analysis. To the extent that motion is present within the blood sample, it will predominantly be that due to Brownian motion of the blood sample's formed constituents, which motion is not disabling of the use of the device of this invention.

The colorant (e.g., a dye, stain, etc.), which is admixed with at least a portion of the blood sample, facilitates identification and quantitative analysis of the constituents (e.g., platelets, WBCs, etc.) that absorb the colorant. The colorant fluoresces along characteristic wavelengths (e.g., 530 nm, 585 nm, and 660 nm) when excited by light along certain wavelengths (e.g., about 470 nm). The specific wavelengths at which a constituent will fluoresce are a characteristic of that constituent and the wavelength(s) of the exciting light. In some embodiments, the colorant can also absorb light at one or more predetermined wavelengths as a function of the concentration of the colorant within the constituent. Examples of acceptable colorants include the supravital dyes acridine orange and astrozone orange. The invention is not limited to supravital dyes, however. A person of skill in the art would know appropriate concentration ranges of colorants, or could determine the same without undue experimentation.

Figure 1:
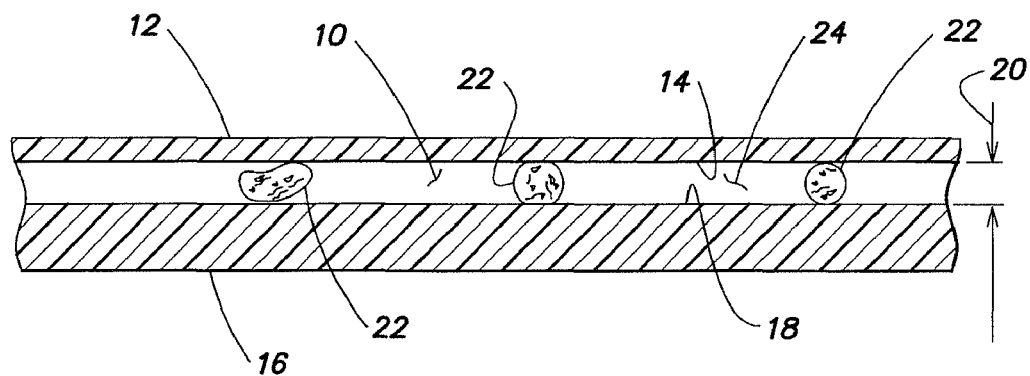
FIGS. 1-4 are cross-sectional diagrammatic representations of analysis chambers that may be used in the present method.
Figure 2:
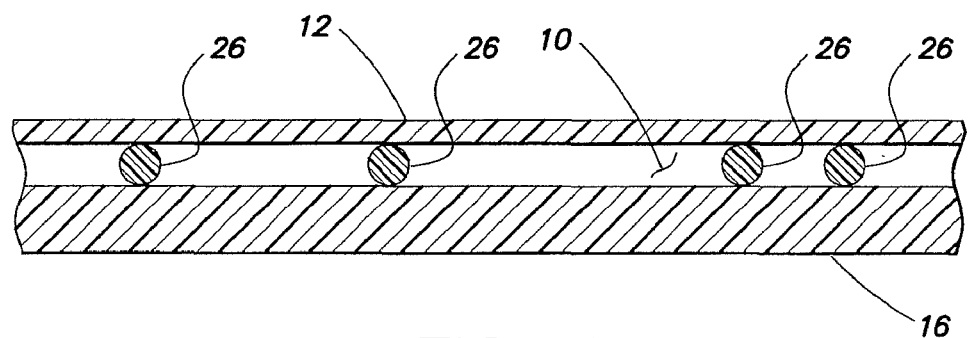

Now referring to FIG. 1, the analysis chamber 10 is defined by a first panel 12 having an interior surface 14, and a second panel 16 having an interior surface 18. The panels 12, 16 are both sufficiently transparent to allow the transmission of light along predetermined wavelengths there through in an amount sufficient to perform the optical density analysis described below. At least a portion of the panels 12, 16 are parallel with one another, and within that portion the interior surfaces 14, 18 are separated from one another by a height 20, which height may be known or measurable. RBCs 22 are shown disposed within the chamber 10.

The present method can utilize a variety of different analysis chambers types having the aforesaid characteristics, and is not therefore limited to any particular type of analysis chamber. An analysis chamber having parallel panels 12, 16 simplifies the analysis and is therefore preferred, but is not required for the present invention; e.g., a chamber having one panel disposed at a known non-parallel angle relative to the other panel could be used.

Now referring to FIGS. 2-5, an example of an acceptable chamber 10 is shown that includes a first panel 12, a second panel 16, and at least three separators 26 disposed between the panels 12, 16. The separators 26 can be any structure that is disposable between the panels 12, 16, operable to space the panels 12, 16 apart from one another. The dimension 28 of a separator 26 that extends between the panels 12, 16 is referred to herein as the height 28 of the separator 26. The heights 28 of the separators 26 typically do not equal one another exactly (e.g., manufacturing tolerances), but are within commercially acceptable tolerance for spacing means used in similar analysis apparatus. Spherical beads are an example of an acceptable separator 26 and are commercially available from, for example, Bangs Laboratories of Fishers, Ind., U.S.A.

Figure 3:
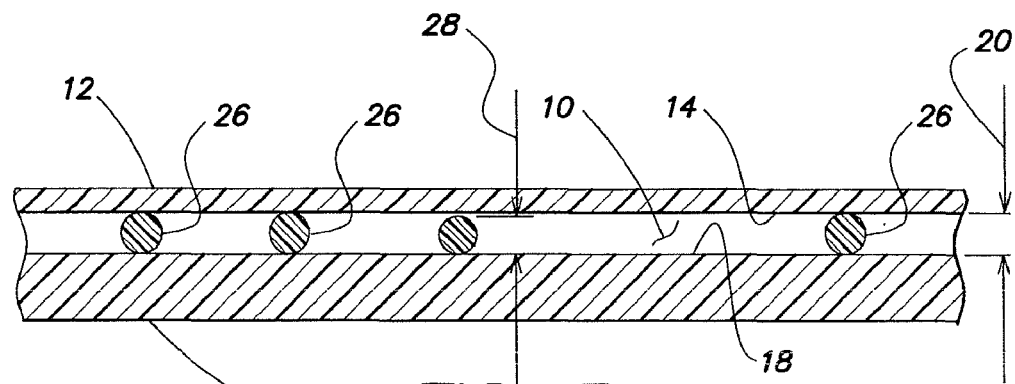
Figure 4:
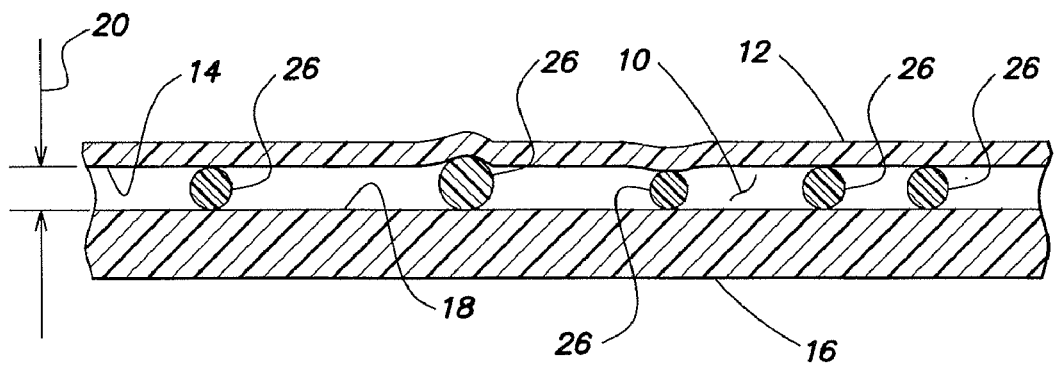
Figure 5:
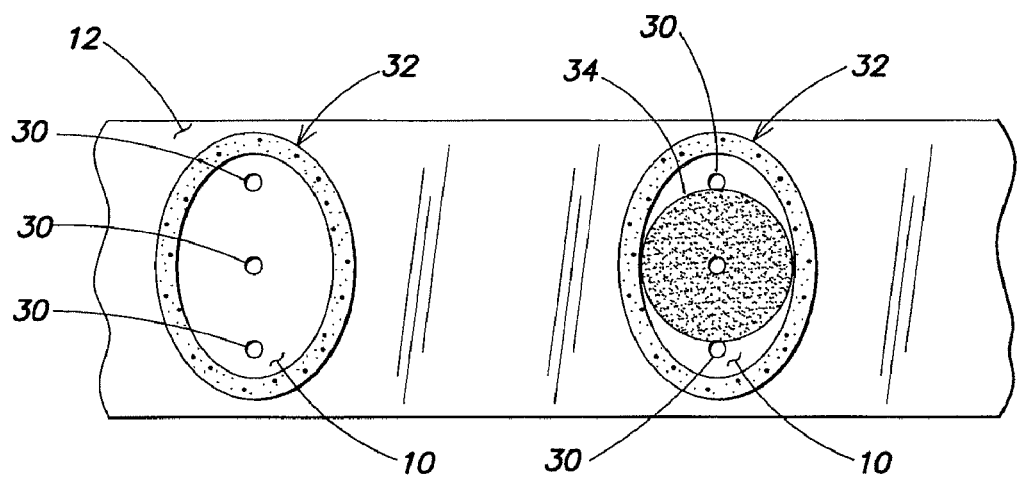
FIG. 5 is a diagrammatic planar view of a tape having a plurality of analysis chambers.

In the chamber embodiment shown in FIG. 3, the separators 26 consist of a material that has greater flexibility than one or both of the first panel 12 and the second panel 16. As can be seen in FIG. 3, the larger separators 26 are compressed to the point where most separators 26 are touching the interior surfaces of the panels 12, 16, thereby making the chamber height just slightly less than the mean separator 26 diameters. In the chamber embodiment shown in FIG. 4, the separators 26 consist of a material that has less flexibility than one or both of the first panel 12 and the second panel 16. In FIG. 4, the first panel 12 is formed from a material more flexible than the spherical separators 26 and the second panel 16, and will overlay the separators 26 in a tent-like fashion. In this embodiment, although small local regions of the chamber 10 may deviate from the desired chamber height 20, the average height 20 of the chamber 10 will be very close to that of the mean separator 26 diameter. Analysis indicates that the mean chamber height 20 can be controlled to one percent (1%) or better at chamber heights of less than four microns using this embodiment. Subject to the flexibility characteristics described above (as well as other factors such as the distribution density of the separators), the separators 26 and panels 12, 16 can be made from a variety of materials, provided the panels 12, 16 are sufficiently transparent. Transparent plastic films consisting of Polyethylene terephthalate is an example of acceptable panels 12, 16, and spherical beads made of polystyrene, polycarbonate, silicone, and the like, are acceptable separators 26. A specific example of an acceptable separator is spheres made of polystyrene that are commercially available, for example, from Thermo Scientific of Fremont, Calif., U.S.A., catalogue no. 4204A, in four micron (4 μm) diameter. Referring to FIG. 5, the panel 12 that is to be vertically disposed above the other includes a plurality of ports 30 disposed at regular intervals (e.g., that act as air vents), and the panels 12, 16 are bonded together at points. In some embodiments, the bonding material 32 forms an outer chamber wall operable to laterally contain the sample 34 within the analysis chamber 10. This example of an acceptable analysis chamber is described in greater detail in U.S. Patent Application Publication Nos. 2007/0243117, 2007/0087442, and U.S. Provisional Patent Application Nos. 61/041,783, filed Apr. 2, 2008; and 61/110,341, filed Oct. 31, 2008, all of which are hereby incorporated by reference in their entirety.

Figure 6:
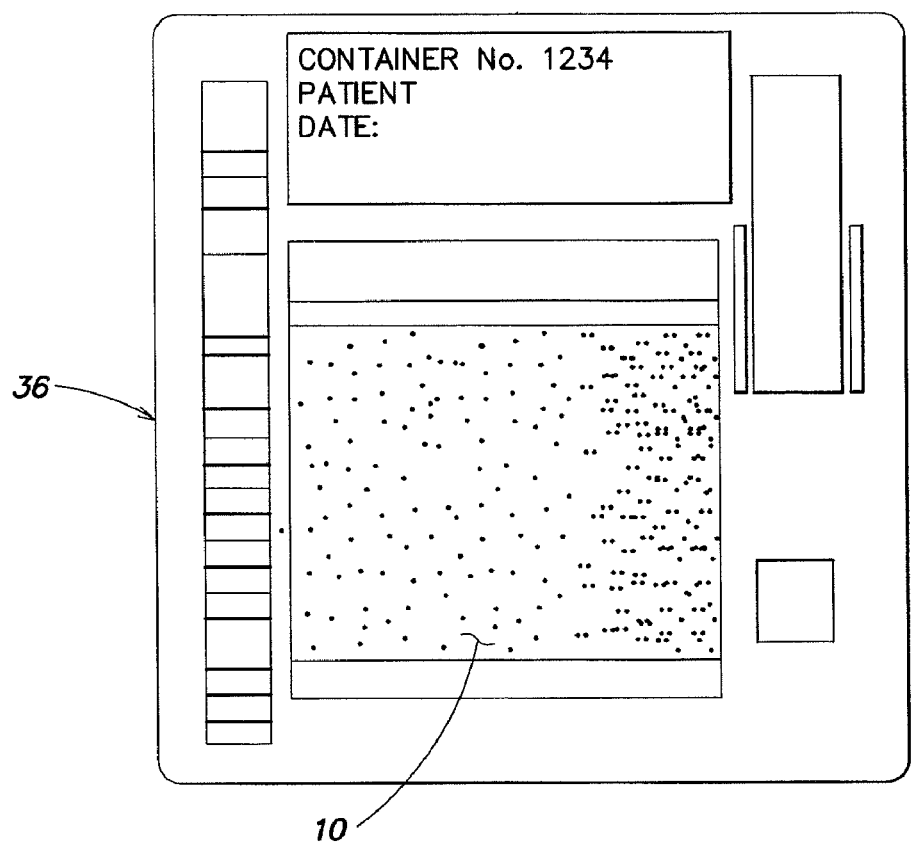
FIG. 6 is a diagrammatic planar view of a disposable container having an analysis chamber.
Figure 7:
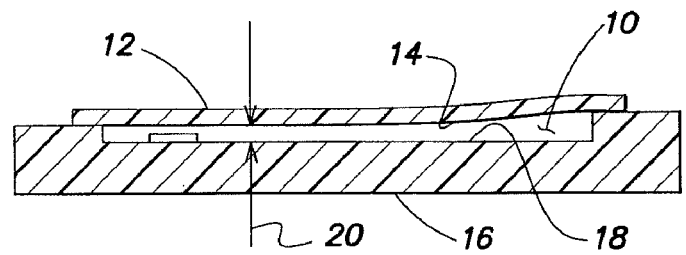
FIG. 7 is a diagrammatic cross-sectional view of a disposable container having an analysis chamber.

Another example of an acceptable chamber 10 is disposed in a disposable container 36 as shown in FIGS. 6 and 7. The chamber 10 is formed between a first panel 12 and a second panel 16. Both the first panel 12 and the second panel 16 are transparent to allow light to pass through the chamber 10. At least a portion of the first panel 12 and the second panel 16 are parallel with one another, and within that portion the interior surfaces 14, 18 are separated from one another by a height 20. This chamber 10 embodiment is described in greater detail in U.S. Pat. No. 6,723,290, which patent is hereby incorporated by reference in its entirety. The analysis chambers shown in FIGS. 2-7, represent chambers that are acceptable for use in the present method. The present method is not, however, limited to these particular embodiments.

It is not necessary to know the exact height of the chamber for purposes of the present disclosure. A chamber height of about two to six microns (2-6μ) is acceptable for most animal species based on typical cell sizes. A chamber height 20 of about three to five microns (3-5μ) is particularly well suited for analyzing human blood. The present invention is not, however, limited to any particular chamber height provided the methodology described herein can be accomplished with such chamber height.

The analysis of the sample quiescently disposed within the chamber 10 is performed using an analysis device that is operable to illuminate and image at least a portion of the sample and perform an analysis on the image. The image is produced in a manner that permits fluorescent emissions from, and the optical density of, the portion of the sample to be determined on a per unit basis. The term "per unit basis" or "image unit" means a defined incremental unit of which the image of the sample can be dissected. A pixel, which is generally defined as the smallest element of an image that can be individually processed within a particular imaging system, is an example of an image unit, and an image unit may include a small number of pixels in a collective unit. The magnification of an imaging device can also be described in linear terms (e.g., microns per pixel at the focal plane), where the linear dimension is along a particular axis of an orthogonal grid applied to the image. The actual area of the sample captured by pixels of the sensor at the focal plane is therefore a function of the magnification factor applied by the imaging device. Hence, it is useful but not required to know the magnification of the imaging device. The volume associated with that pixel is therefore the area of the image per pixel times the chamber height. For example if the magnification was 0.5 microns per pixel, an image occupying 200 pixels would have an area of 50 square microns, and a volume of 50 square microns times the chamber height.

Figure 8:
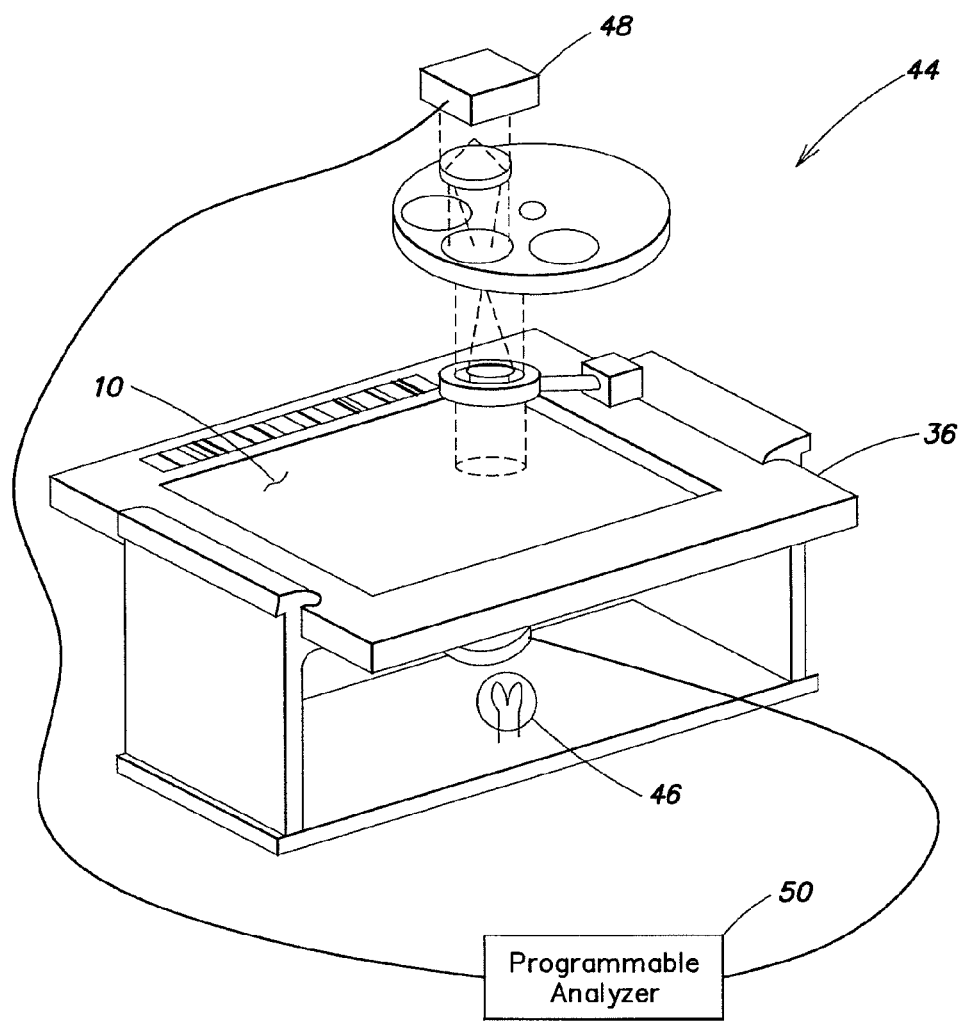
FIG. 8 is a diagrammatic schematic of an analysis device that may be used with the present method.

Now referring to FIG. 8, an example of an analysis device 44 that can be adapted for use with the present method includes a sample illuminator 46, an image dissector 48, and a programmable analyzer 50. The sample illuminator 46 includes a light source that selectively produces light along certain desired wavelengths. For example, LEDs that emit the desired wavelengths (e.g., 420 nm, 440 nm, 470 nm, etc.) can be used. Alternatively, a light source that produces a broad wavelength range (e.g., approximately 400-670 nm) can be used, although in some instances such a light source may require filtering. The analysis device 44 may include optics for manipulating the light. The sample illuminator 46 includes a transmittance light source and an epi-illumination light source, each operable to illuminate some, or all, of the sample residing within the chamber 10. An example of an acceptable image dissector 48 is a charge couple device (CCD) type image sensor that converts an image of the light passing through the sample into an electronic data format (i.e., a signal). Complementary metal oxide semiconductor ("CMOS") type image sensors are another example of an image sensor that can be used, and the present invention is not limited to either of these examples. The programmable analyzer 50 includes a central processing unit (CPU) and is connected to the sample illuminator 46 and image dissector 48. The CPU is adapted (e.g., programmed) to selectively perform the functions necessary to perform the present method. It should be noted that the functionality of programmable analyzer 50 may be implemented using hardware, software, firmware, or a combination thereof. A person skilled in the art would be able to program the processing unit to perform the functionality described herein without undue experimentation. U.S. Pat. No. 6,866,823 entitled "Apparatus for Analyzing Biologic Fluids" and issued Mar. 15, 2005, which is hereby incorporated by reference in its entirety, discloses such an analysis device 44.

The analysis device is adapted to process the image signals created from the illumination of at least a portion of the sample to identify and enumerate constituents within the sample. The image signals include fluorescent emissions and optical density values on a per pixel basis. The intensity and color of the emissions and the optical density per pixel collectively establish the image of the illuminated sample portion. Within the collective image, the analysis device is adapted to identify a profile of selected constituents, using one or more of the fluorescent intensity, color content, and optical density of the fluorescent emissions, and in some instances physical characteristics (e.g., area, edge geometry, etc.) of the constituents. The analysis device uses the image profiles to distinguish amongst the selected constituents until the remaining constituents represent the target constituents (e.g., platelets), at which point the target constituents can be enumerated.

Under the present method, a sample of substantially undiluted whole blood is introduced into a chamber 10, and thereinafter resides quiescently within the chamber 10. An anticoagulating agent and a colorant are admixed with the sample either prior to its introduction into the chamber or upon introduction into the chamber. The colorant is absorbed by the constituents (e.g., WBCs, platelets, reticulocytes) within the sample. In some applications, an isovolumetric sphering agent is added to the sample to cause some or all of the RBCs within the sample to assume a spherical-like shape. An example of an acceptable isovolumetric sphering agent is a zwitterionic detergent. A specific example of a sphering agent is Zwittergent® 3-16 detergent, which is a zwitterionic detergent produced by Calibriochem, an entity of EMD Chemicals, Inc. of New Jersey, U.S.A. The amount of sphering agent added to the sample is an amount adequate to sphere at least a number of RBCs required to perform the present hematocrit analysis. The specific amount will depend on the particular agent and test circumstances, which can be determined by a person of skill in the art without undue experimentation. The natural bioconcave shape of RBCs, and the relative size of RBCs relative to platelets, can cause platelets within a sample to be "hidden" amongst the RBCs in the sample; e.g., within the concavities of an RBC. Sphering the RBCs decreases the likelihood of platelets being hidden within a sample amongst the RBCs and increases the likelihood that such platelets can be viewed as individuals within the plasma, and thereby increases the accuracy of quantitative platelet analyses performed on the sample.

At least a portion of the sample quiescently residing within the chamber is illuminated by the analysis device 44, which transmits light through the sample. Although it is not a requirement that the entire sample residing within the chamber be imaged, it is preferable since doing so typically provides a more complete analysis of the sample and a concomitant increase in accuracy. The sample is illuminated with wavelengths known to excite a fluorescent emission from the constituents relating to the colorant absorbed by the constituents. Constituents stained with acridine orange produce a fluorescent emission when illuminated with violet light at a wavelength of about 470 nm. The photographs shown in FIGS. 9-13 illustrate the fluorescent emissions of constituents (e.g., platelets, giant platelets, WBCs, reticulocytes, platelet clumps) found within the sample. The specific emissions depend upon the colorant used and the intracellular composition of the illuminated cell (e.g., interaction of the colorant with contents of the cell or platelet creates the emissions). Some constituents have fluorescent emissions that act as a fluorometric signature (also referred to as a "profile"), which signature represents a particular ratio of fluorescent emissions along wavelengths that produce combinations of light (e.g., a characteristic "red/green" ratio) that are relatively unique to that constituent and can therefore be used to identify that constituent. Other constituents have fluorescent emission signatures that cannot easily be distinguished from one another. To distinguish those constituents, the sample is illuminated with wavelengths of light that are absorbed by hemoglobin in appreciably greater amounts than would be absorbed by the platelets or plasma. The amount of absorption can be measured in terms of optical density, and the optical density in turn can be used to distinguish constituents containing hemoglobin from those that do not.

Figure 9:
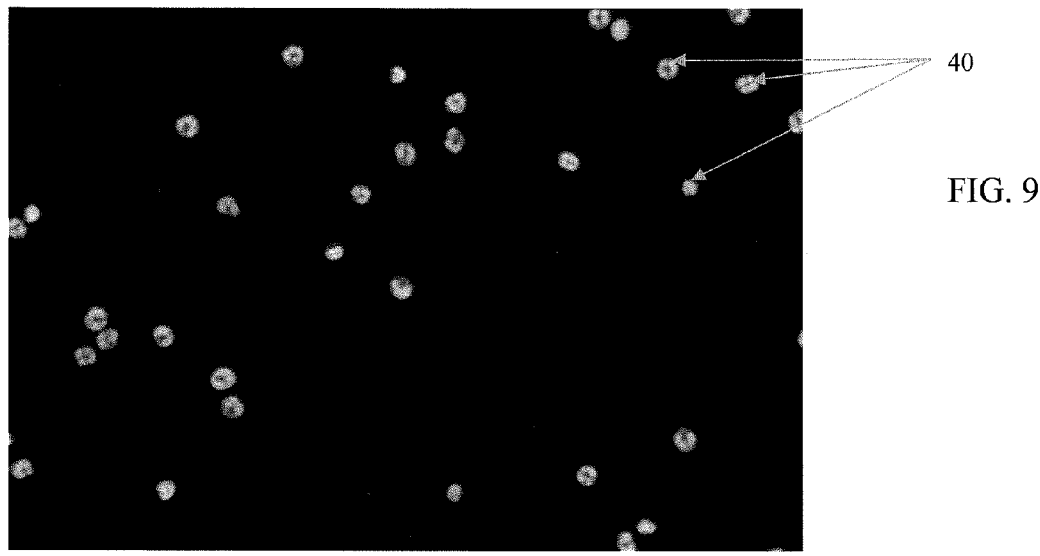
FIG. 9 is a color image of a portion of a chamber containing a substantially undiluted blood sample admixed with a acridine orange fluorescent dye, that has been illuminated at a wavelength that produces fluorescent emissions from constituents (e.g., WBCs, platelets, etc) that have absorbed the dye, imaged at a first intensity amplification.
Figure 10:
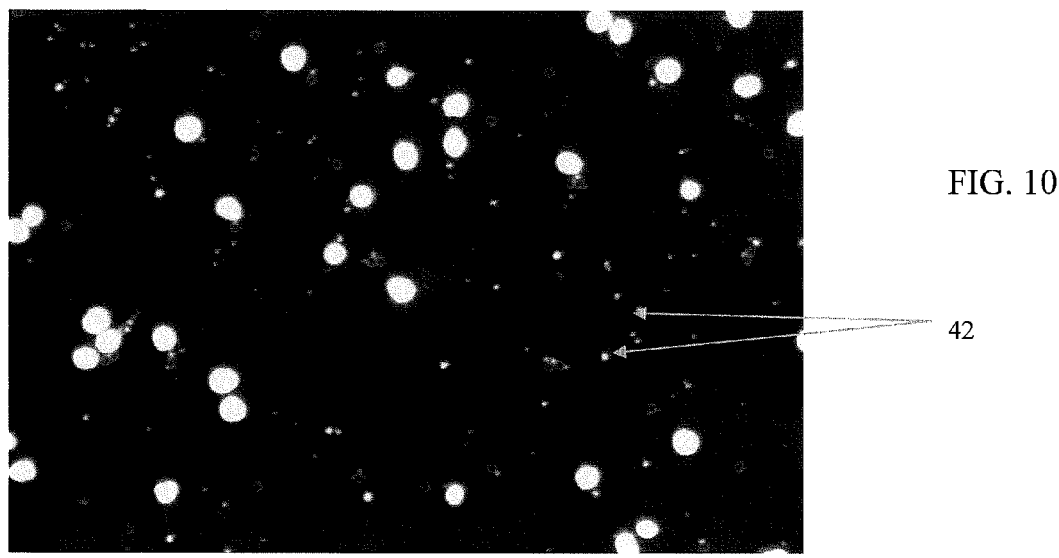
FIG. 10 is the color image shown in FIG. 9, imaged at a second intensity amplification that is greater than the first.

Because the fluorescent emission portion of the image is a function of factors such as the type of colorant used and the concentration of the colorant within the sample, it is useful, but not required, to calibrate the sample for intensity. For example, for a given concentration of colorant, the fluorescent emission from WBCs is on average higher than the fluorescent emission from platelets. This can be clearly seen in FIGS. 9 and 10, which are images of the same sample. The amplification of the fluorescent emission in FIG. 10 is greater than that used in FIG. 9. FIG. 9 clearly shows the fluorescent emissions from the WBCs 40, and faintly shows the emissions from the platelets 42. FIG. 10 clearly shows both WBCs 40 and platelets 42, and also shows how each can be distinguished by their fluorescent emission intensity. The calibration identifies the intensity level associated with the WBCs and the intensity level associated with the platelets to the analysis device, and calibrates the analysis device accordingly.

The fluorescent emissions and transmitted light produced by illuminating the sample are converted into image signals on a per pixel basis that collectively establish the image of the illuminated sample portion. Within the collective image, the analysis device is adapted to identify a profile of certain selected constituents, using one or more of the fluorescent intensity, color content, and optical density of the fluorescent emissions. The process of identifying the constituents profiles via aforesaid characteristics can be performed using algorithms that compare the various characteristics to identify the constituent Once the constituent is identified, it can be further analyzed. For example, a representative number of platelets can be identified within the sample via their fluorescent emission profile and collectively analyzed to determine an average of the fluorescent emission intensity for the platelets. In some instances, constituent fluorescent profiles are also used to determine the internal areas and edge regions of the constituents using the fluorescent signal profiles. The areas of individual constituents can be averaged to determine an average area value. The edge profiles can be analyzed for smoothness and/or for geometry; e.g., determine if the edge of a constituent is circular, non-circular, irregular, etc. These characteristics are subsequently used to distinguish constituents within the sample, until the remaining constituents represent the target constituents (e.g., platelets), at which point the target constituents can be enumerated.

To illustrate an example of the present invention, a substantially undiluted sample of blood is admixed with EDTA, acridine orange, and a zwitterionic detergent and is introduced within a chamber having two transparent panels for the purpose of determining a platelet count within the sample. Constituents, including RBCs, reticulocytes, WBCs, platelets, giant platelets, and platelet clumps, reside quiescently within the sample. The sample is illuminated at 470 nm, at least one of 413 nm and 540 nm. The 470 nm illumination produces a fluorescent emission from the acridine orange. Other colorants may emit light upon illumination at other wavelengths. The 413 nm and/or 540 nm illumination is used to indicate the presence of hemoglobin by its optical density, as will be discussed below. Digital images of the illuminated sample are taken.

The image of the sample is analyzed to identify various constituents disposed within the sample. WBCs, for example, are individually identified by one or more of their fluorescent signature (e.g., fluorescent emission pattern consisting of a significant red cytoplasmic fluorescence and a green nuclear fluorescence), the relative intensity of their fluorescent emissions, the area they occupy, and their shape (see FIGS. 9-11). The WBCs are thereby distinguished from the remainder of the sample; e.g., by filtering the image so that WBCs are no longer considered within the image.

Figure 12:
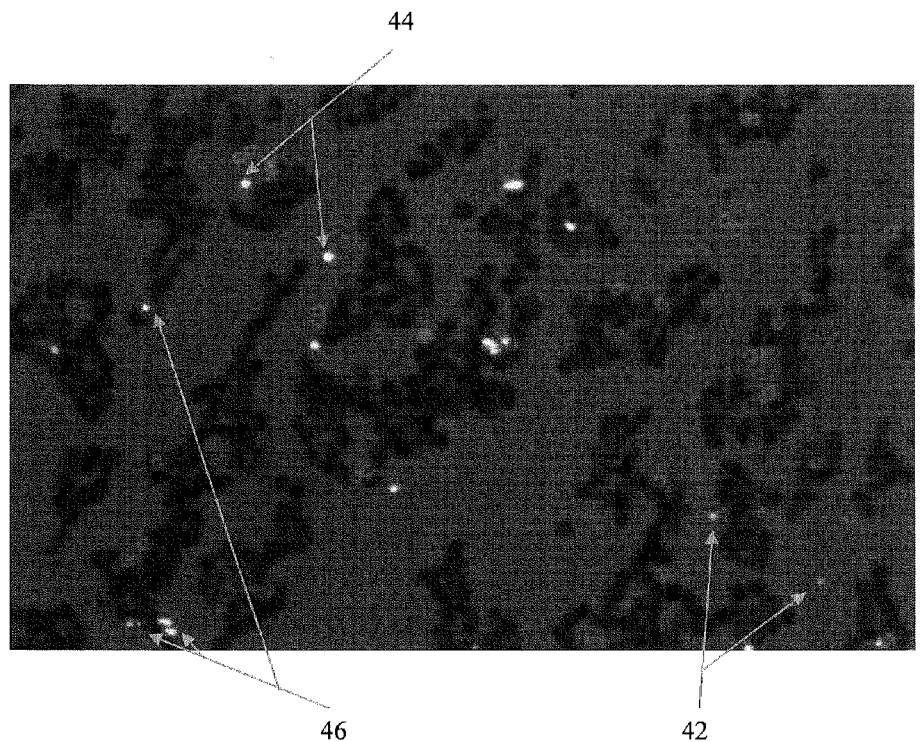
FIG. 12 is a color image of a portion of a chamber containing a substantially undiluted blood sample admixed with a acridine orange fluorescent dye, that has been illuminated at a wavelength that produces fluorescent emissions from constituents, illustrating the different emission profiles of platelets, giant platelets, and reticulocytes.

Now referring to FIG. 12, giant platelets 44 can be identified within the sample by one or more of their fluorescent profile, area, and shape. RBCs 45 can be seen faintly in the background. The colorimetric ratio of a giant platelet 44 is similar to that of a normal platelet 42, but the emissions are greater in intensity due to the larger mass of the particle. Giant platelets 44 are also significantly larger than normal platelets 42 and circular in size. Normal platelets 42 are typically irregularly shaped. Most normal sized platelets are 1.5 to 3 µm in diameter. Giant platelets 44, in contrast, are larger than 7 µm and usually in the range of 10 µm to 20 µm in diameter. The identification and enumeration of giant platelets provides important clinical information, since the presence of giant platelets may be an indicator of Bernard-Soulier syndrome and myeloproliferative disorders (e.g., chronic myelogenous leukemia (CML), polycythemia vera, essential (primary) thrombocythemia, and agnogenic myeloid metaplasia). Giant platelets 44 within the sample are identified by comparing one or more of their fluorescent emissions (colorimetric and intensity), area, and perimeter shape against normal platelet fluorescent emission values, area, and perimeter shapes, including the average platelet intensity and area values. As an example of criteria that can be used to identify giant platelets, the analysis device can be programmed with one or more comparative criteria relative to normal platelets (e.g., a multiple of the average platelet area or intensity based on standard deviations of the average normal platelet area or intensity, or by a predetermined area or intensity value, etc.). With respect to with average platelet area, the distribution of platelet areas within any given sample is typically described as a log-normal function and can be determined statistically using known techniques. The identified giant platelets are then distinguished and, depending upon the specific information desired, are included in the platelet count and/or are considered as an independent constituent population.

Figure 13:
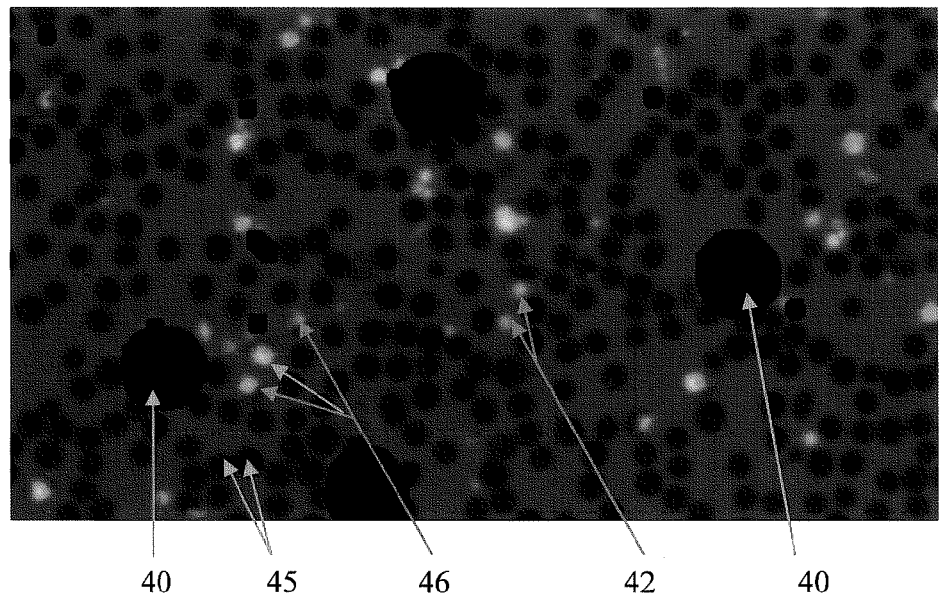
FIG. 13 is a color image of a portion of a chamber containing a substantially undiluted blood sample admixed with a acridine orange fluorescent dye, that has been illuminated at a wavelength that produces fluorescent emissions from constituents, illustrating the different emission profiles of platelets and reticulocytes. The image also includes WBCs edited from the image, and RBCs faintly seen in the background.
Figure 14:
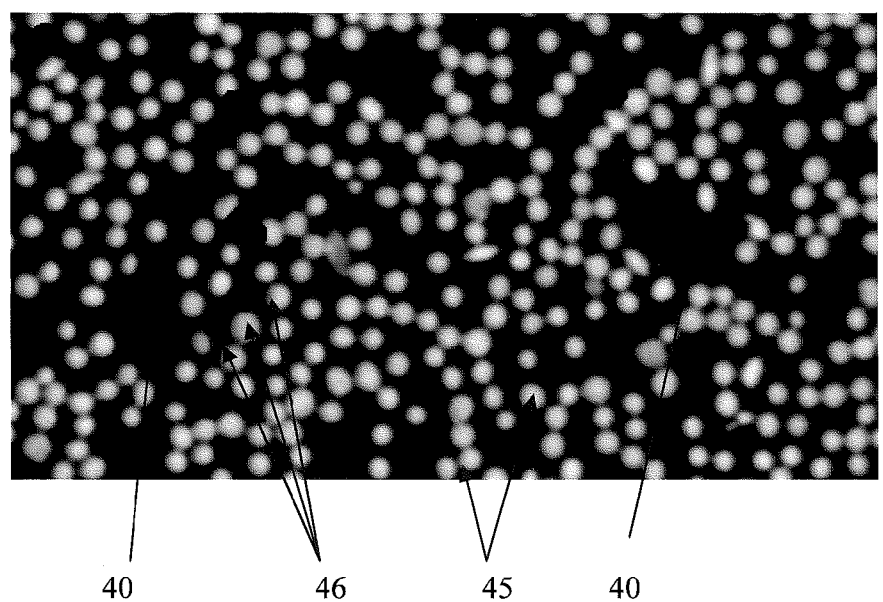
FIG. 14 is a black and white version of the image shown in FIG. 13 which is created by illuminating the sample at a wavelength that shows the optical density values of the image. This image illustrates the optical density profiles of reticulocytes and RBCs within the sample, which profiles enables reticulocytes to be identified.
Figure 15:
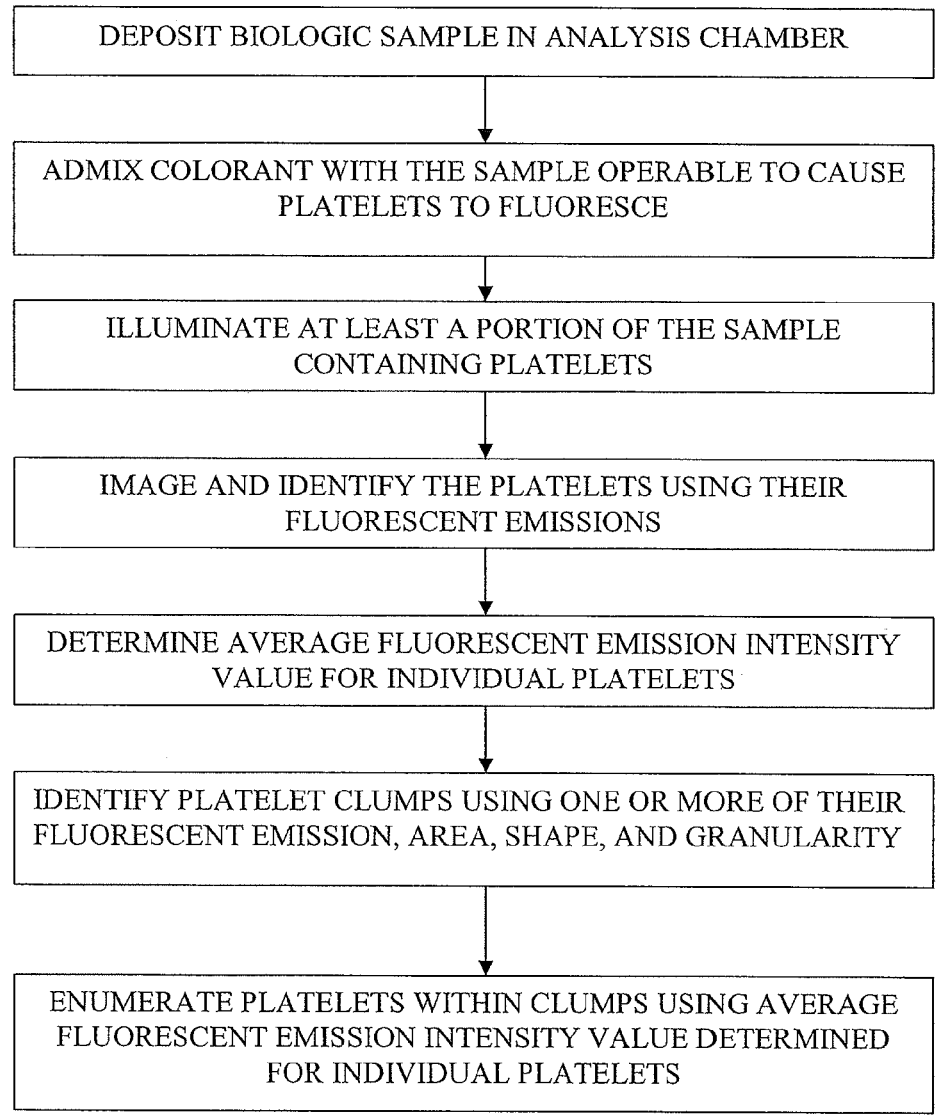
FIG. 15 is a block diagram of the steps a method according to an aspect of the present invention.

Reticulocytes 46 emit a fluorescent profile that is similar to that of normal platelets because of the nuclear material they contain. The photograph in FIG. 13 shows the fluorescent emissions of reticulocytes 46 and platelets 42. The circular blacked out portions are portions of the image where WBCs were disposed, but which image was masked out. The reticulocytes 46 can be distinguished from platelets 42 to some extent by their fluorescent emission, which appears slightly brighter and has slightly more red. The reticulocytes 46 can also be distinguished by illuminating the sample with light at wavelengths of 413 nm and/or 540 nm, which wavelengths are absorbed by the hemoglobin to a substantially greater amount than any other material present within the sample and is, therefore, indicative of the presence of hemoglobin. The light absorption of the hemoglobin can be quantified in terms of optical density. FIG. 14 illustrates the OD of the reticulocytes. The reticulocytes are distinguished from the remainder of the sample using one or both of the fluorescent emission patterns and OD.

Figure 11:
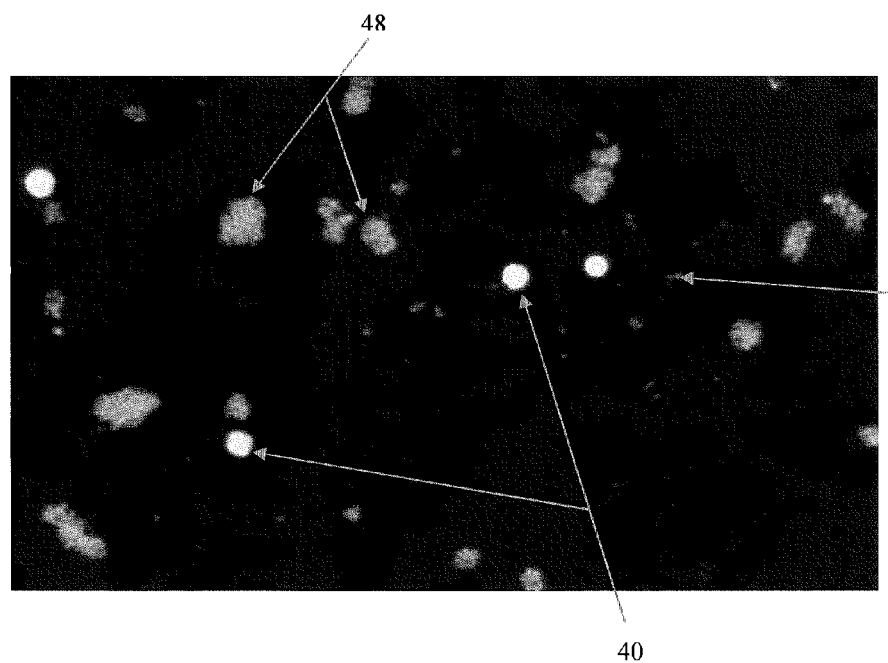
FIG. 11 is a color image of a portion of a chamber containing a substantially undiluted blood sample admixed with a acridine orange fluorescent dye, that has been illuminated at a wavelength that produces fluorescent emissions from constituents, illustrating the different emission profiles of WBCs, platelet clumps, and platelets.

In most blood samples, the constituents with a fluorescent emission remaining after the WBCs, giant platelets, and reticulocytes have been distinguished are predominantly, if not entirely, platelets. Individual platelets within the sample can be identified and enumerated. In some blood samples, however, a portion of the platelets within the sample may be aggregated into one or more clumps, which clumps can be very large in size; e.g., one to four times the size of a WBC. The photograph in FIG. 11 shows both platelet clumps 48 and WBCs 40. The platelet clumps 48 are identifiable and distinguishable from other constituents (e.g., WBCs 40, giant platelets 44) by their fluorescent emission profile which has a red/green ratio that is distinguishable from that of a WBC 40, by their granularity, and in some instances by their area and/or shape. For example, platelet clumps 48 are distinguishable from giant platelets because platelet clumps are irregular shaped and giant platelets are substantially circularly shaped. The relative circularity of both platelet clumps and giant platelets can be determined by image analysis software programmed into analysis device. Detecting the presence of platelet clumps within the sample is important because of the possibility that the clumps will be counted as WBCs (and thereby falsely elevate the WBC count) and/or lead to a false diagnosis of thrombocytopenia. These potential problems are particularly relevant with existing automated analyzers. The presence of platelet clumps can be an indicator of inadequate mixing of the sample with EDTA.

Once a platelet clump is identified, the integrated fluorescent emission intensity of the clump and the area of the clump can be determined. The number of platelets within the clump can then be determined by dividing the integrated fluorescent emission intensity by the average platelet emission intensity. The quotient value is an acceptable approximation of the actual number of platelets within the clump. An approximation of the number of platelets within a clump can also be determined by dividing the area of the clump by the average platelet area.

Although this invention has been shown and described with respect to the detailed embodiments thereof, it will be understood by those skilled in the art that various changes in form and detail may be made without departing from the spirit and scope of the invention.

What is claimed is:

1. A method for enumerating platelets within a blood sample, comprising the steps of:

depositing the sample into a sample container having an analysis chamber adapted to quiescently hold the sample for analysis, and an amount of colorant that platelets absorb and which fluoresces upon exposure to one or more predetermined first wavelengths of light;

imaging at least a portion of the sample disposed in the analysis chamber, including producing image signals indicative of fluorescent emissions from the platelets illuminated by first wavelengths of light;

identifying the platelets using the image signals, and one or more of area, shape, and granularity characteristics; and enumerating individual platelets within the sample.

2. The method of claim 1, wherein the step of identifying the platelets includes identifying giant platelets within the sample.

3. The method of claim 2, wherein the step of identifying the platelets includes determining an average area for the individual platelets identified within the sample, and comparing a determined area of at least one giant platelet identified within the sample to the average platelet area.

4. The method of claim 2, wherein the step of identifying giant platelets within the sample includes comparing the area of at least one giant platelet to a predetermined value.

5. A method for enumerating platelets within a blood sample, which sample is disposed in an analysis chamber adapted to quiescently hold the sample for analysis, and which sample includes an amount of colorant that platelets absorb and which fluoresces upon exposure to one or more predetermined first wavelengths of light, the method comprising the steps of:

imaging at least a portion of the sample disposed in the analysis chamber, including producing image signals indicative of fluorescent emissions from the platelets illuminated by first wavelengths of light;

identifying the platelets using the image signals, and one or more of area, shape, and granularity characteristics; and enumerating platelets within the sample.

6. The method of claim 5, wherein the platelets enumerated within the sample include one or more of individual platelets, clumped platelets and giant platelets.

7. An apparatus for enumerating platelets within a blood sample, which sample includes a colorant operative to cause the platelets to fluoresce upon exposure to one or more predetermined first wavelengths of light, the apparatus comprising:

an analysis chamber adapted to quiescently hold the sample for analysis, the chamber defined by a first panel and a second panel;

an imaging unit that is operable to image at least a portion of the sample and produce image signals indicative of fluorescent emissions from the platelets; and a programmable analyzer adapted to identify and enumerate platelets within the sample, using the image signals, and area, shape, and granularity characteristics.

8. The apparatus of claim 7, wherein the programmable analyzer is further adapted to determine a total number of platelets within the sample as a sum of platelets within one or more platelet clumps and platelets individually residing within the sample.

9. The apparatus of claim 7, wherein the programmable analyzer is adapted to identify giant platelets within the sample.

10. The apparatus of claim 9 wherein the programmable analyzer is adapted to identify giant platelets within the sample by one or more of fluorescent emissions, area, and shape.

11. The apparatus of claim 7, wherein the imaging unit is operable to image at least a portion of the sample and produce second image signals indicative of an optical density of one or more constituents within the sample; and wherein the programmable analyzer is adapted to determine the optical density of at least one of the constituents within the sample using the second image signals, and to distinguish the platelets and the constituents from one another using the determined optical density.

* * * * *